United States Patent [19]

Alig et al.

[11] 4,028,400

[45] June 7, 1977

[54] D-HOMOSTEROIDS

[76] Inventors: Leo Alig, 76 Heidenlochstrasse, Liestal; Andor Fürst, 14 Magnolienpark, Basel; Peter Keller, 10 Bahnhofstrasse, Therwil; Marcel Müller, 10 Quellenweg, Frenkendorf, all of Switzerland; Ulrich Kerb, 8 Waitzstrasse; Rudolf Wiechert, 5 Petzower Strasse, both of Berlin, Germany

[22] Filed: Sept. 20, 1974

[21] Appl. No.: 507,884

[30] Foreign Application Priority Data

Sept. 26, 1973 Switzerland ............... 13762/73

[52] U.S. Cl. ............... 260/488 B; 260/326.33; 260/340.5; 260/340.9; 260/348 A; 260/408; 260/410; 260/456 R; 260/468 R; 260/476 C; 260/586 E; 424/278; 424/305; 424/308; 424/311; 424/312; 424/331
[51] Int. Cl.² .................................... C07J 63/00
[58] Field of Search ........... 260/488 B, 586 E, 410, 260/468 R, 476 C

[56] References Cited

UNITED STATES PATENTS

| 2,822,381 | 2/1958 | Dodson et al. | 260/488 B |
| 2,860,158 | 11/1958 | Clinton | 260/488 B |
| 3,076,023 | 1/1963 | Raspar et al. | 260/586 E |
| 3,492,338 | 1/1970 | Hader et al. | 260/488 B |
| 3,833,621 | 9/1974 | Grunwell et al. | 260/586 E |

FOREIGN PATENTS OR APPLICATIONS

| 2,309,328 | 10/1963 | Germany | 260/488 B |
| 146,774 | 5/1969 | New Zealand | 260/488 B |

OTHER PUBLICATIONS

Chem. Abstracts, 80:37392g.
Chem. Abstracts, 49:6299d.
Chem. Abstracts, 52:11980a.

*Primary Examiner*—Vivian Garner
*Attorney, Agent, or Firm*—Samuel L. Welt; George M. Gould

[57] ABSTRACT

The present invention relates to steroids. More particularly, the invention is concerned with D-homosteroids, a process for the manufacture thereof and pharmaceutical preparations containing same.

18 Claims, No Drawings

D-HOMOSTEROIDS

DETAILED DESCRIPTION OF THE INVENTION

The D-homosteroids provided by the present invention have the following general formula:

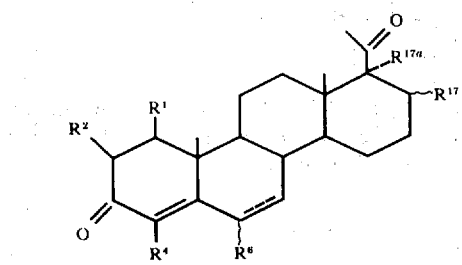

wherein $R^1$ and $R^2$ each represent a hydrogen atom or together represent a $1\alpha,2\alpha$-methylene group or a C—C bond, $R^4$ represents a hydrogen or chlorine atom, $R^6$ represents a hydrogen, fluorine, chlorine or bromine atom or a methyl group, $R^{17}$ represents a hydrogen atom or a methyl, methylene, acyloxy or alkoxy group and $R^{17a}$ represents a methyl or acyloxy group or $R^{17}$ and $R^{17a}$ together represent a group of the formula

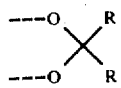

in which each R independently represents a hydrogen atom or a lower alkyl or phenyl group or one R represents a lower alkoxy group, and wherein the broken line in the 6,7-position denotes an optional C-C bond.

An acyloxy group can be derived from a saturated or unsaturated aliphatic carboxylic acid, a cycloaliphatic, araliphatic or an aromatic carboxylic acid preferably containing up to 15 carbon atoms. Examples of such acids are formic acid, pivalic acid, propionic acid, butyric acid, caproic acid, oenanthic acid, undecylenic acid, oleic acid, cyclopentylpropionic acid, cyclohexylpropionic acid, phenylacetic acid and benzoic acid. The preferred acyloxy groups are alkanoyloxy groups containing from 1 to 7 carbon atoms. The alkoxy groups can be straight-chain or branched-chain groups preferably containing up to 15 carbon atoms. Lower alkoxy groups are especially preferred. The lower alkyl and lower alkoxy groups preferably contain from 1 to 4 carbon atoms, especially methyl and ethyl or methoxy and ethoxy.

An alkyl group present in the 17-position and, in the case of 6,7-saturated D-homosteroids, a substituent present in the 6-position, can have the $\alpha$- or $\beta$-configuration. The $\alpha$-isomers are preferred.

Acording to the process provided by the present invention, the D-homosteroids of formula I hereinbefore are manufactured by a. oxidising the 3-hydroxy-$\Delta^5$ grouping in a D-homosteroid of the general formula

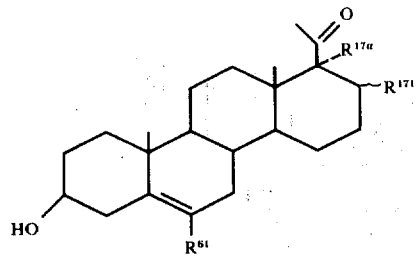

, wherein $R^{61}$ represents a hydrogen atom or a methyl group, $R^{171}$ represents a hydrogen atom or a methyl, acyloxy or alkoxy group and $R^{17a}$ represents a methyl or acyloxy group or $R^{17a}$ and $R^{171}$ together present a group of the formula

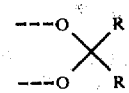

in which R has the significance given earlier, to the 3-keto-$\Delta^4$, 3-keto-$\Delta^{4,6}$ or 3-keto-$\Delta^{1,4,6}$ grouping, or b. dehydrogenating a D-homosteroid of the general formula

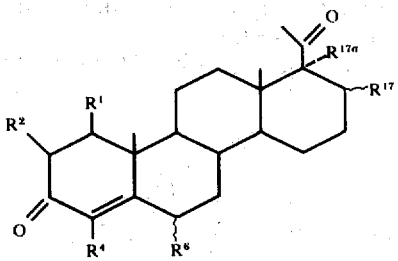

, wherein $R^1$, $R^2$, $R^4$, $R^6$, $R^{17}$ and $R^{17a}$ have the significance given earlier,
in the 1,2-and/or 6,7-position in the case where $R^1$ and $R^2$ each represent a hydrogen atom, or in the 6,7-position in the case where $R^1$ and $R^2$ together represent a $1\alpha,2\alpha$-methylene group of a C-C bond, or dehydrogenating a 6-dehydro derivative of a D-homosteroid of formula III in which $R^1$ and $R^2$ each represent a hydrogen atom in the 1,2-position, or c. fluorinating, chlorinating or brominating a D-homosteroid of the general formula

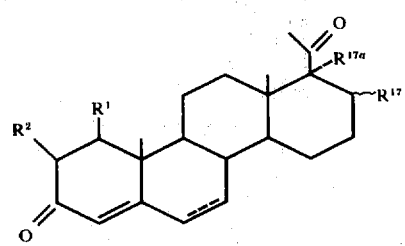

, wherein $R^1$, $R^2$, $R^{17}$, $R^{17a}$ and the broken line in the 6,7-position have the significance given earlier, in the 6-position and, if desired, isomerising a $6\beta$-isomer obtained to the $6\alpha$-isomer, or d. methylating a D-homosteroid of the general formula

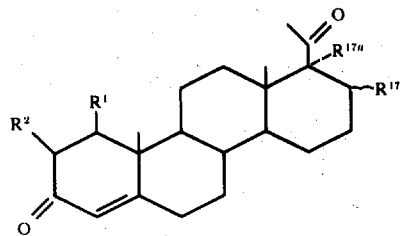

, wherein $R^1$, $R^2$, $R^{17}$ and $R^{17a}$ have the significance given earlier,
in the 6-position, or e. chlorinating a D-homosteroid of the general formula

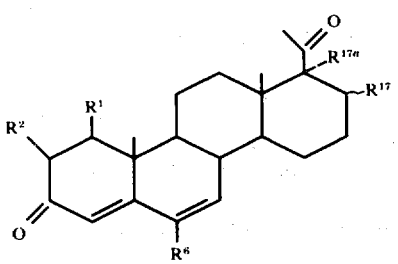

, wherein $R^1$, $R^2$, $R^6$, $R^{17}$ and $R^{17a}$ have the significance given earlier, in the 4-position, or f. acylating the hydroxy group(s) in a D-homosteroid of the general formula

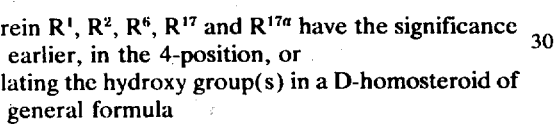

, wherein $R^1$, $R^2$, $R^4$, $R^6$ and the broken line in the 6,7-position have the significance given earlier and $R^{172}$ represents a hydrogen atom or a methyl, methylene, hydroxy, acyloxy or alkoxy group,
or g. adding a methylene group to the 1,2-double bond of a D-homosteroid of the general formula

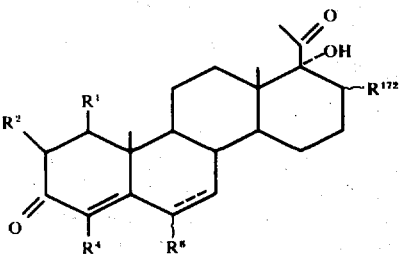

, wherein $R^6$, $R^{17}$, $R^{17a}$ and the broken line in the 6,7-position have the significance given earlier, h. converting the 17,17a-dihydroxy grouping in a D-homosteroid of the general formula

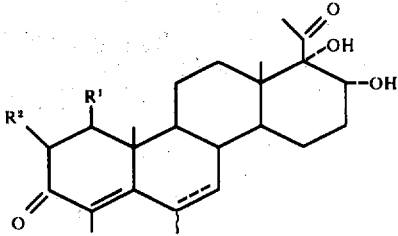

, wherein $R^1$, $R^2$, $R^4$, $R^6$ and the broken line in the 6,7-position have the significance given earlier,
into a ketal group of the formula

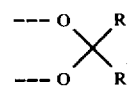

in which R has the significance given earlier,
or i. subjecting a D-homosteroid of the general formula

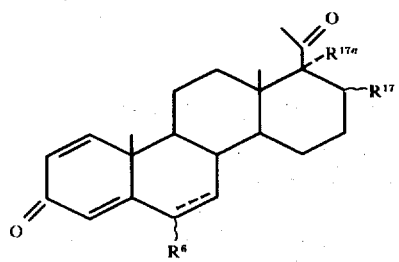

, wherein $R^{17}$ and $R^{17a}$ have the significance given earlier, $R^5$ represents a fluorine, chlorine or bromine atom or a hydroxy group and $R^{62}$ represents a fluorine, chlorine or bromine atom or a methyl group,
to a $HR^5$ cleavage.

The oxidation of a D-homosteroid of formula II in accordance with embodiment a) of the present process can be carried out according to the Oppenauer procedurre (e.g. by means of aluminium isopropylate), or with an oxidising agent such as chromium trioxide (e.g. Jones' reagent), or according to the Pfitzner-Moffatt procedure by means of dimethyl sulphoxide/dicyclohexylcarbodiimide (the initially obtained $\Delta^5$-3-ketone requiring subsequent isomerisation to the $\Delta^4$-3-ketone), or using pyridine/sulfur trioxide. When one of the previously mentioned oxidising agents is used, there is obtained a D-homosteroid containing a 3-keto-$\Delta^4$ grouping. When an oxidising agent such as $Br_2$/LiBr-/$Li_2CO_3$ in dimethylformamide is used or when the oxidation is carried out according to the Oppenauer procedure in the presence of benzoquinone, the oxidation yields a D-homosteroid containing a 3-keto-$\Delta^{4,6}$ grouping. 2,3-Dichloro-5,6-dicyano-benzoquinone is, for example, suitable for the oxidation to a D-homosteroid containing a 3-keto-$\Delta^{1,4,6}$ grouping.

The 1,2-dehydrogenation of a D-homosteroid of formula III in accordance with embodiment b) of the present process can be carried out in a manner known per se; for example, in a microbiological manner or using a dehydrogenating agent such as selenium dioxide, 2,3-dichloro-5,6-dicyano-benzoquinone, chloranil, thallium triacetate or lead tetraacetate. Suitable microorganisms for the 1,2-dehydrogenation are, for example, Schizomycetes, especially those of the genera Arthrobacter (e.g. A. simplex ATCC 6946), Bacillus (e.g. B.lentus ATCC 13805 and B. sphaericus ATCC 7055), Pseudomonas (e.g. P. aeruginosa IFO 3505), Flavobacterium (e.g. F. flavescens IFO 3058), Lactobacillus (e.g. L. brevis IFO 3345) and Nocardia (e.g. N. opaca ATCC 4276).

The introduction of a $\Delta^6$-double bond into a D-homosteroid of formula III can be carried out, for example, using a substituted-benzoquinone such as chloranil [see J.Am. Chem. Soc. 82, 4293 (1960); 81, 5951 (1959)] or using 2,3-dichloro-5,6-dicyano-benzoquinone or using manganese dioxide [see J. Am. Chem. Soc. 75, 5932 (1953)].

A 1,4,6-trisdehydro-D-homosteroid can be obtained directly from a D-homosteroid of formula III in which $R^1$ and $R^2$ each represent a hydrogen atom using 2,3-dichloro-5,6-dicyano-benzoquinone or chloranil.

The halogenation of a D-homosteroid of formula IV in the 6-position in accordance with embodiment c) of the present process can be carried out in a manner known per se. A 6,7-saturated D-homosteroid of formula IV can be halogenated by treatment with a halogenating agent such as a N-haloamide or imide (e.g. N-bromoacetamide, N-bromosucinimide or N-chlorosuccinimide) or with elementary bromine or chlorine [see J.Am. Chem. Soc. 72, 4534 (1950)]. The halogenation in the 6-position is preferably carried out by converting a 6,7-saturated D-homosteroid of formula IV into a 3-enol ester or 3-enol ether (e.g. the 3-enol acetate) followed by treatment with chlorine or bromine [see J.Am.Chem.Soc. 82, 1230 (1960); 77, 3827 (1955)] or with perchloryl fluoride [see J.Am.-Chem.Soc. 81, 5259 (1959); Chem. and Ind. 1959, 1317]. Trifluoromethylhypofluorite can also be used as a fluorinating agent.

The halogenation in the 6-position can also be carried out by converting a 4,6-bisdehydro- or 1,4,6-trisdehydro-D-homosteroid of formula IV into a 6α,7α-epoxide (e.g. by treatment with a peracid such as perphthalic acid, m-chloroperbenzoic acid or p-nitroperbenzoic acid), treating the 6α,7α-epoxide with an appropriate hydrogen halide and cleaving off water from the resulting 7-hydroxy-6-halo-D-homosteroid with the elimination of the 7-hydroxy group and the introduction of a 6,7-double bond. Furthermore, the chlorination can be carried out using chromyl chloride in methylene chloride or ethers.

Insofar as the halogenation described earlier yields mixtures of isomers (i.e. mixtures of 6α- and 6β-halo-D-homosteroids), these mixtures can be separated into the pure isomers according to methods known per se such as chromatography.

The isomerisation of a 6β-halo-D-homosteroid, especially a 6β-(fluoro or chloro)-D-homosteroid, obtained can be carried out by treatment with an acid, especially a mineral acid such as hydrochloric acid, or hydrobromic acid in a solvent such as dioxane or glacial acetic acid.

The methylation in accordance with embodiment d) of the present process can be carried out, for example, by converting a D-homosteroid of formula V into a 3-enol ether (e.g. by treatment with a formic acid ester such as ethyl orthoformate in the presence of an acid such as p-toluenesulphonic acid, if desired with the addition of the corresponding alcohol, or by treatment with a dialkoxypropane such as 2,2-dimethoxypropane in methanol/dimethylformamide in the presence of p-toluenesulphonic acid) and reacting the enol ether with a tetrahalomethane (e.g. $CBr_4$, $CCl_2Br_2$ or $CCl_3Br$) to give a trihalomethyl-$\Delta^4$-3-ketone. A trihalomethyl-$\Delta^4$-3-ketone can be dehydrohalogenated with a base such as collidine to give a dihalomethylene-$\Delta^4$-3-ketone which, in turn, can be converted into a 6α-methyl-$\Delta^4$-3-ketone by catalytic hydrogenation under mild conditions (e.g. in the presence of a palladium/strontium carbonate catalyst).

An advantageous procedure for the methylation of D-homosteroids of formula V in which $R^1$ and $R^2$ each represent a hydrogen atom comprises converting a D-homosteroid of formula V into a 3-enol ether in the manner described earlier, converting the 3-enol ether in a manner known per se into a corresponding 6-formyl derivative, reducing the formyl group to the hydroxymethyl group using sodium borohydride and then dehydrating the reduction product with cleavage of the enol ether to give a 6-methylene-D-homosteroid of the general formula

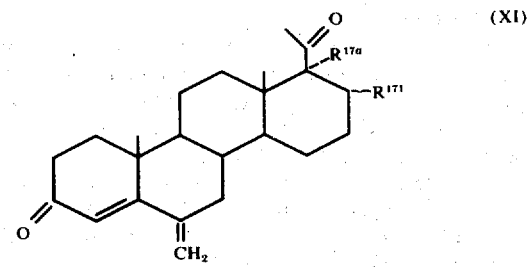

(XI)

wherein $R^{171}$ and $R^{17a}$ have the significance given earlier.

6-Methylene-D-homosteroids of formula XI can also be prepared by converting a D-homosteroid of formula V into a 3-enamine (e.g. the 3-pyrrolidinium-enamine), hydroxymethylation with formaldehyde and dehydration with an acid such as p-toluenesulphonic acid.

The isomerisation of a 6-methylene-D-homosteroid of formula XI to give a D-homosteroid containing a 6-methyl-$\Delta^6$ grouping can be carried out in a manner known per se; for example, catalytically. Suitable isomerisation catalysts are, for example, metal catalysts which are also used, for example, in hydrogenations, especially palladium in ethanol. A hydrogen donator such as cyclohexane is expediently also added as an activator for the catalyst. Undesired side-reactions such as hydrogenations by the hydrogen donator can be avoided by buffering the mixture. Furthermore, the 6-methylene-D-homosteroids can be hydrogenated in the usual manner using known hydrogenation catalysts to give the desired 6-methyl-D-homosteroids.

The chlorination in accordance with embodiment e) of the present process is expediently carried out by introducing chlorine or sulphuryl chloride into a medium which contains a D-homosteroid of formula VI. The chlorination can be carried out in the presence of a proton acceptor; for example, a N,N-di(lower alkyl)-(lower alkanoyl)amide such as dimethylformamide or dimethylacetamide or a lower alkylene oxide such as ethylene oxide or propylene oxide in a solvent such as a lower alkanecarboxylic acid (e.g. propionic acid or acetic acid). Alternatively, the chlorination can be carried out in the absence of a proton acceptor. In this case, the initial chlorination product is subsequently treated with one of the aforementioned proton acceptors or with a nitrogen-containing heterocylic base such as picoline or pyridine.

The acylation of the 17a-hydroxy group in a D-homosteroid of formula VII in accordance with embodiment f) of the present process can be carried out in a manner known per se by treatment with a reactive acid derivative such as an acyl halide or acid anhydride in the presence of the acid corresponding to the acylating agent and a strong acid such as p-toluenesulphonic acid, perchloric acid or a mineral acid (e.g. hydrochloric acid). Where the D-homosteroid of formula VII contains a hydroxy group in the 17-position, then this is concomitantly acylated under the aforementioned conditions. It is, however, also possible to acylate the hydroxy group present in the 17-position before the hydroxy group present in the 17a-position in a manner known per se using a milder acylating agent (e.g. using pyridine/acid anhydride at room temperature).

The 1,2-methylenation in accordance with embodiment g) of the present process can be carried out according to methods known per se for the addition of a methylene group to a double bond with the formation of a cyclopropyl-condensed ring system. It can be carried out, for example, according to the Corey procedure using dimethylsulphoxonium methylide. In this procedure, a D-homosteroid of formula VIII is reacted, for example, with a solution prepared from trimethylsulphoxonium iodide and sodium hydride in dimethylsulphoxide. The 1,2-methylenation can also be carried out, for example, by treating a D-homosteroid of formula VIII with diazomethane and thermally decomposing the intermediate obtained.

The ketalisation of the 17,17a-dihydroxy grouping in a D-homosteroid of formula IX in accordance with embodiment h) of the present process can be carried out in a manner known per se by reacting a D-homosteroid of formula IX with an appropriate aldehyde, ketone or ortho ester, acetaldehyde, acetone, methyl ethyl ketone, benzophenone, acetophenone, methyl orthoformate or ethyl orthoformate in the presence of a catalytic amount of an acid such as perchloric acid or p-toluenesulphonic acid.

The cleavage of $HR^5$ from a D-homosteroid of formula X in accordance with embodiment i) of the present process, i.e. a dehydration or a dehydrohalogenation, can be carried out in a manner known per se. The dehydration can be carried out by treatment with an acid (e.g. a mineral acid such as hydrochloric acid) or with a base. The dehydrohalogenation can be carried out using a base (e.g. an organic base such as pyridine).

Examples of D-homosteroids of formula I hereinbefore are:

17A-acetoxy-6α-chloro-D-homo-4-pregnene-3,20-dione, 17a-acetoxy-6α-fluoro-D-homo-4-pregnene-3,20-dione, 17a-acetoxy-6α-bromo-D-homo-4-pregnene-3,20-dione, 17a-acetoxy-6α-methyl-D-homo-4-pregnene-3,20-dione, 17a-acetoxy-D-homo-4-pregnene-3,20-dione, 17a-acetoxy-6α-chloro-D-homo-1,4-pregnadiene-3,20-dione, 17a-acetoxy-6α-fluoro-D-homo-1,4-pregnadiene-3,20-dione, 17a-acetoxy-6α-bromo-D-homo-1,4-pregnadiene-3,20-dione, 17a-acetoxy-6α-methyl-D-homo-1,4-pregnadiene-3,20-dione, 17a-acetoxy-D-homo-1,4-pregnadiene-3,20-dione, 17a-acetoxy-6-chloro-D-homo-4,6-pregnadiene-3,20-dione, 17a-acetoxy-6-fluoro-D-homo-4,6-pregnadiene-3,20-dione, 17a-acetoxy-6-bromo-D-homo-4,6-pregnadiene-3,20-dione, 17a-acetoxy-6-methyl-D-homo-4,6-pregnadiene-3,20-dione, 17a-acetoxy-D-homo-4,6-pregnadiene-3,20-dione, 17a-acetoxy-6-chloro-D-homo-1,4,6-pregnatriene-3,20-dione, 17a-acetoxy-6-fluoro-D-homo-1,4,6-pregnatriene-3,20-dione, 17a-acetoxy-6-bromo-D-homo-1,4,6-pregnatriene-3,20-dione, 17a-acetoxy-6-methyl-D-homo-1,4,6-pregnatriene-3,20-dione, 17a-acetoxy-D-homo-1,4,6-pregnatriene-3,20-dione, 17a-acetoxy-6α-chloro-1,2-methylene-D-homo-4-pregnene-3,20-dione, 17a-acetoxy-6α-fluoro-1,2-methylene-D-homo-4-pregnene-3,20-dione, 17-a-acetoxy-6α-bromo-1,2-methylene-D-homo-4-pregnene-3,20-dione, 17a-acetoxy-6α-methyl-1,2-methylene-D-homo-4-pregnene-3,20-dione, 17a-acetoxy-1,2-methylene-D-homo-4-pregnene-3,20-dione, 17a-acetoxy-6-chloro-1,2-methylene-D-homo-4,6-pregnadiene-3,20-dione, 17a-acetoxy-6-bromo-1,2-methylene-D-homo-4,6-pregnadiene-3,20-dione, 17a-acetoxy-6-fluoro-1,2-methylene-D-homo-4,6-pregnadiene-3,20-dione, 17a-acetoxy-6-methyl-1,2-methylene-D-homo-4,6-pregnadiene-3,20-dione, 17a-acetoxy-1,2-methylene-D-homo-4,6-pregnadiene-3,20-dione, 6α-chloro-17a-methyl-D-homo-4-pregnene-3,20-dione, 6α-bromo-17a-methyl-D-homo-4-pregnene-3,20-dione, 6α-fluoro-17a-methyl-D-homo-4-pregnene-3,20-dione, 6α,17a-dimethyl-D-homo-4-pregnene-3,20-dione, 17a-methyl-D-homo-4-pregnene-3,20-dione, 6-chloro-17a-methyl-D-homo-1,4-pregnadiene-3,20-dione, 6-bromo-17a-methyl-D-homo-1,4-pregnadiene-3,20-dione, 6-fluoro-17a-methyl-D-homo-1,4-pregnadiene-3,20-dione, 6,17a-dimethyl-D-homo-1,4-pregnadiene-3,20-dione, 17a-methyl-D-homo-1,4-pregnadiene-3,20-dione, 6-chloro-17a-methyl-D-homo-4,6-pregnadiene-3,20-dione, 6-bromo-17a-methyl-D-homo-4,6-pregnadiene-3,20-dione, 6-fluoro-17a-methyl-D-homo-4,6-pregnadiene-3,20-dione, 6,17a-dimethyl-D-homo-4,6-pregnadiene-3,20-dione, 17a-methyl-D-homo-4,6-pregnadiene-3,20-dione, 6α-chloro-17a-methyl-D-homo-1,4,6-pregnatriene-3,20-dione, 6α-bromo-17a-methyl-D-homo-1,4,6-pregnatriene-3,20-dione, 6α-fluoro-17a-methyl-D-homo-1,4,6-pregnatriene-3,20-dione,
6α,17a-dimethyl-D-homo-1,4,6-pregnatriene-3,20-dione,
17a-methyl-D-homo-1,4,6-pregnatriene-3,20-dione,
6α-chloro-17a-methyl-1,2-methylene-D-homo-4-pregnene-3,20-dione,
6α-bromo-17a-methyl-1,2-methylene-D-homo-4-pregnene-3,20-dione,
6α-fluoro-17a-methyl-1,2-methylene-D-homo-4-pregnene-3,20-dione,
6α,17a-dimethyl-1,2-methylene-D-homo-4-pregnene-3,20-dione,
17a-methyl-1,2-methylene-D-homo-4-pregnene-3,20-dione,
6-chloro-17a-methyl-1,2-methylene-D-homo-4,6-pregnadiene-3,20-dione,
6-bromo-17a-methyl-1,2-methylene-D-homo-4,6-pregnadiene-3,20-dione,
6-fluoro-17a-methyl-1,2-methylene-D-homo-4,6-pregnadiene-3,20-dione,
6,17a-dimethyl-1,2-methylene-D-homo-4,6-pregnadiene-3,20-dione and
17a-methyl-1,2-methylene-D-homo-4,6-pregnadiene-3,20-dione.

A preferred class of D-homosteroids of formula I hereinbefore comprises those in which $R^1$, $R^2$, $R^4$ and $R^{17}$ each represent a hydrogen atom and $R^{17a}$ represents an acryloxy group. Moreover, those D-homosteroids of formula I in which $R^6$ represents a chlorine atom or a methyl group and $R^{17a}$ represents an alkanoyloxy group containing from 1 to 7 carbon atoms are also preferred.

The D-homosteroid starting materials used in the present process, insofar as their preparation has not yet been described, can be prepared in a manner analogous to that described in the Examples hereinafter. The preparation of the D-homosteroid starting materials of formula II can be carried out in the manner illustrated in the following formula scheme by way of example of 17a-acetoxy-3-hydroxy-D-homo-5-pregnen-20-one (IIa):

sequent epoxidation of the 17,20-double bond with a peracid, basic hydrolysis and acylation yields the 17-methyl derivative of a compound of formula (5), the 3-acetoxy group of which can be saponified in a known manner.

A 6-methyl-D-homosteroid starting material of formula II can be prepared, for example, as follows:

A 3,17a-dihydroxy-D-homopregn-5-en-20-one obtained by saponifying the 3-acyloxy group in a compound of formula (4) is ketalised in the 20-position, the 3-hydroxy group is then converted by solvolysis of the 3-mesylate or 3-tosylate (e.g. in acetone in the presence of potassium acetate) to give the corresponding i-D-homosteroid, the 6-hydroxy group of which is then oxidised by means of a Jones' reagent to give the 6-ketone. Reaction of this ketone with a methyl-Grignard reagent followed by acidic hydrolysis yields a 3,17a-dihydroxy-6-methyl-D-homo-preg-5-en-20-one, from which the 6-methyl derivative of a compound of formula (IIa) is obtained by acylation and partial hydrolysis as shown in steps (4) → (5) → (IIa) of the foregoing formula scheme.

Alternatively, a 6-methyl group can be introduced into a D-homosteroid starting material of formula II in the following manner:

A compound of formula (5) is ketalised in the 20-position and HOBr is added to the 5,6-double bond. The resulting 3,17a-diacetoxy-20,20-ethylenedioxy-5α-bromo-6-hydroxy-pregnane can be oxidised with Jones' reagent to give the 6-ketone and this can be reduced by means of Raney nickel to give 3,17a-diacetoxy-20,20-ethylenedioxy-pregnan-6-one which yields the desired 6-methyl-D-homosteroid starting material upon reaction with a methyl-Grignard compound and water-cleavage.

A 17a-methyl group can be introduced into a compound (1) in a manner known per se by reaction with lithium in ammonia and subsequent reaction with methyl iodide.

Methyl groups can also be introduced into the 6- and 17-position of a D-homosteroid of formula IIa in the

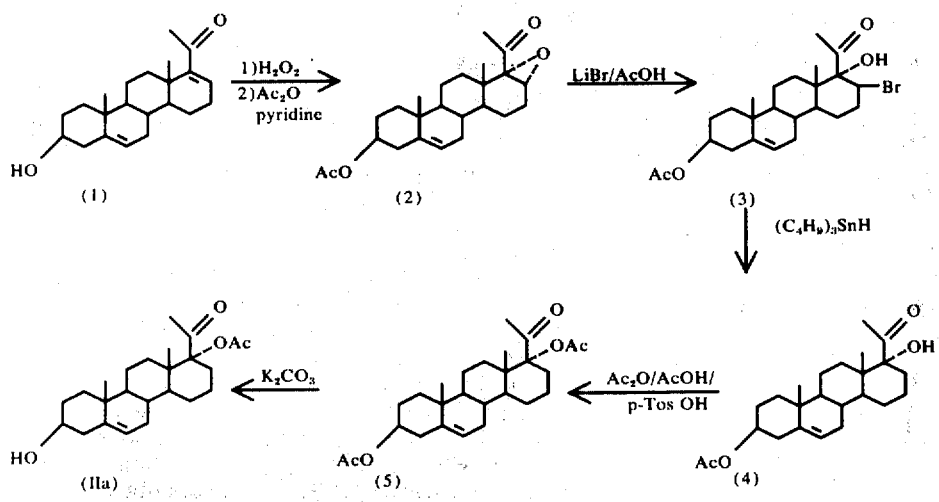

A 17-methyl-D-homosteroid starting material of formula II can be prepared, for example, by acetylating a compound of formula (1) of the foregoing formula scheme, reacting the acetylated product with a methyl-Grignard reagent in the presence of copper (I) chloride and acetylating and resulting magnesium enolate. Subfollowing manner:

A compound of formula (1) is treated with a peracid, the resulting 5α,6α-epoxide is reacted with a methyl-Grignard reagent in the presence of copper (I) chloride and the resulting magnesium enolate is acetylated. Treatment of the enol acetate with a peracid, basic hydrolysis, oxidation of the resulting 3β,5α,17a-trihydroxy-6,17-dimethyl-pregnan-20-one with Jones' reagent and dehydration yields 17α-hydroxy-6,17αdimethyl-pregn-4-ene-3,20-dione which can be converted by acylation into a D-homosteroid starting material of formula III in which $R^1$, $R^2$ and $R^4$ each represent a hydrogen atom, $R^6$ and $R^{17}$ each represent a methyl group and $R^{17a}$ represents an acyloxy group.

D-Homosteroid starting material of formula X in which $R^5$ represents a hydroxy group can be prepared by converting a corresponding 3-keto-$\Delta^4$-D-homosteroid into the 3,3-ethylene ketal, epoxidising this ketal with a peracid (e.g. m-chloroperbenzoic acid), chromatographically separating the 5α,6α-epoxide from the reaction mixture and opening the epoxide by treatment with a boron halide such as boron trifluoride (in order to introduce a halogen atom into the 6-position) or with a methyl-Grignard reagent (in order to introduce a methyl group into the 6-position) and finally hydrolysing the 3-ketal group. D-Homosteroid starting materials of formula X in which $R^5$ represents a halogen atom can be prepared by converting a corresponding 3-keto-$\Delta^4$-D-homosteroid into the 3,3-ethylene ketal and treating this ketal with chlorine, bromine or bromofluorine.

The D-homosteroids of formula 1 hereinbefore possess hormonal activity, especially on the endocrinal system. Their activity is selective. They may accordingly be used as hormonally active agents (e.g. as progestational agents) and may be administered orally or parenterally. Typical dosages may range, for example, from 0.005 mg/kg to 0.15 mg/kg per day.

The D-homosteroids of formula 1 can be used as medicaments; for example, in the form of pharmaceutical preparations which contain them in association with a compatible pharmaceutical carrier. This carrier can be an organic or inorganic inert carrier material suitable for enteral, percutaneous or parenteral administration such as, for example, water, gelatine, gum arabic, lactose, starch, magnesium stearate, talc, vegetable oils, polyalkyleneglycols, petroleum jelly and the like. The pharmaceutical preparations can be made up in a solid form (e.g. as tablets, dragees, suppositories or capsules), in a semi-solid form (e.g. as salves) or in a liquid form (e.g. as solutions, suspensions or emulsions). The pharmaceutical preparations may be sterilised and/or may contain adjuvants such as preservatives, stabilisers, wetting agents, emulsifiers, salts for varying the osmotic pressure or buffers. The pharmaceutical preparations may also contain therapeutically valuable materials other than the D-homosteroids provided by the present invention.

The following Examples illustrate the process provided by the present invention:

EXAMPLE 1

25.4 g of 3β-hydroxy-17a-acetoxy-D-homo-5-pregnen-20-one in 508 ml of toluene and 50.8 ml of cyclohexanone are heated to boiling and treated with a solution of 11.6 g of aluminium isopropylate in 100 ml of toluene. The mixture is then heated for a further 2 hours with slow distillation. The cooled solution is diluted with benzene, washed with dilute sulphuric acid and water and evaporated. The residue is chromatographed on silica gel, there being obtained 22.3 g of crude 17a-acetoxy-D-homo-4-pregnen-3,20-dione. A sample recrystallised from diisopropyl ether/methylene chloride melts at 221.5°–223.4° C; UV: $\epsilon_{240} = 1.300$ The starting material can be prepared as follows:

50.0 g of 3β-hydroxy-D-homo-5,17(17a)-pregnadien-20-one are dissolved in 500 ml of methylene chloride, 750 ml of ethanol and 3.5 litres of methanol and the solution is treated at 35° C with 40 ml of 4-N sodium hydroxide and 50 ml of 30% hydrogen peroxide. The mixture is reacted at 35° C for 4 days (40 ml of 30% hydrogen peroxide being added twice daily), the solution is then extensively concentrated in vacuo at 35° C, subsequently diluted with methylene chloride and washed free from hydrogen peroxide with water. After drying over sodium sulphate, the solution is evaporated to dryness in vacuo and the residue stirred in 200 ml of pyridine and 100 ml of acetic anhydride for 30 minutes at 60° C. The precipitate obtained after precipitation with ice-water is filtered off under suction, washed well with water, taken up in methylene chloride and dried. After chromatography on silica gel and after recrystallisation from diisopropyl ether, there are obtained 21.3 g of 3β-acetoxy-17α,17a-epoxy-D-homo-5-pregnene-20-one of melting point 161°–163° C.

14.0 g of 3β-acetoxy-17β,17a-epoxy-D-homo-5-pregnen-20-one in 140 ml of acetic acid are treated with 42 g of lithium bromide and stirred at room temperature for 2 days. The mixture is stirred into ice-water, the precipitate filtered off, washed well with water, taken up in methylene chloride and dried. After evaporation, there are obtained 17.4 g of crude 17-bromo-17a-hydroxy-3β-acetoxy-D-homo-5-pregnen-20-one.

17.4 g of crude 17β-bromo-17a-hydroxy-3β-acetoxy-D-homo-5-pregnen-20-one are dissolved in 174 ml of benzene and 174 ml of tetrahydrofuran. 17.4 ml of tributyl tin hydride and 870 mg of α,α'-azoisobutyronitrile are added under a stream of nitrogen and the mixture is stirred for 1.5 hours at 60° C. The mixture is then extensively concentrated in vacuo, the residue treated with pentane, the precipitated off under suction and recrystallised from ethyl acetate. There are thus obtained 11.6 g of 17a-hydroxy-3β-acetoxy-D-homo-5-pregnen-20-one of melting point 208°–210.5° C.

7.25 g of 17a-hydroxy-3β-acetoxy-D-homo-5-pregnen-20-one in 36 ml of acetic acid, 11 ml of acetic anhydride and 1.45 g of p-toluenesulphonic acid are stirred at room temperature for 18 hours. The precipitate obtained after precipitation with ice-water and filtration is taken up in methylene chloride, dried and evaporated. After recrystallisation from methanol, there are obtained 7.1 g of 3β,17a-diacetoxy-D-homo-5-pregnen-20-one of melting point 126-127° C.

7.0 g of 3β,17a-diacetoxy-D-homo-5-pregnen-20-one in 70 ml of methanol and 7 ml of water are treated with 3.5 g of potassium carbonate and heated under reflux for 15 minutes. After precipitation in ice-water weakly acidified with acetic acid, the precipitate is filtered off, taken up in methylene chloride, dried and evaporated. After recrystallisation from diisopropyl ether/methylene chloride, there are obtained 6.7 g of 3β-hydroxy-17a-acetoxy-D-homo-5-pregnen-20-one of melting point 184°–188° C.

EXAMPLE 2

In a manner analogous to that described in Example 1, from 17a-hexanoyloxy-3β-hydroxy-D-homo-5- pregnen-20-one there is obtained 17a-hexanoyloxy-D-homo-4-pregnen-3,20-dione; UV: $\epsilon_{240} = 16500$.

EXAMPLE 3

1.0 g of 17a-acetoxy-D-homo-4-pregnene-3,20-dione in 30 ml of tert butanol are heated under reflux for 7 hours with 1.1 g of chloranil. The mixture is then extensively concentrated in vacuo, the residue taken up in ether, washed with dilute sodium hydroxide and water, dried and evaporated. After chromatography on silica gel and after recrystallisation from diisopropyl ether/methylene chloride, there are obtained 650 mg of 17a-acetoxy-D-homo-4,6-pregnadiene-3,20-dione of melting point 207.5°–209° C; UV: $\epsilon_{284} = 27000$.

EXAMPLE 4

In a manner analogous to that described in Examples 1 and 3, from 17a-decanoyloxy-3β-hydroxy-D-homo-5-pregnen-20-one there is obtained, via 17a-decanoyloxy-D-homo-4-pregnen-3,20-dione, 17a-decanoyloxy-D-homo-4,6-pregnadiene-3,20-dione as an oil; UV: $\epsilon_{284} = 25200$.

EXAMPLE 5

3.4 g of 17a-acetoxy-D-homo-4,6-pregnadiene-3,20-dione in 34 ml of tertbutanol and 8 ml of methylene chloride are treated with 6.8 g of 70% m-chloroperbenzoic acid and the mixture is left to stand at room temperature for 44 hours. The mixture is then concentrated in vacuo, the residue taken up in ether and washed with sodium bisulphite solution, sodium bicarbonate solution and water. The residue obtained after evaporation is chromatographed on silica gel and, after recrystallisation from diisopropyl ether/acetone, there are obtained 950 mg of 17a-acetoxy-6α,7α-epoxy-D-homo-4-pregnene-3,20-dione of melting point 254.5°–259° C; UV: $\epsilon_{240} = 15000$.

200 ml of 17a-acetoxy-6α,7α-epoxy-D-homo-4-pregnene-3,20-dione are added to a solution (cooled to −75° C) of 2.5 ml of hydrogen fluoride in 2.5 ml of dimethylformamide and the mixture is stirred at room temperature for 2 hours. The mixture is then stirred into an excess of potassium bicarbonate solution and extracted with methylene chloride. The residue obtained after evaporation is chromatographed on silica gel, there being obtained 170 mg of 6β-fluoro-7α-hydroxy-17a-acetoxy-D-homo-4pregnene-3,20-dione.

170 mg of crude 6β-fluoro-7α-hydroxy-17a-acetoxy-D-homo-4-pregnene-3,20-dione in 2 ml of pyridine are treated with 0.2 ml of methansulphonic acid chloride and stirred at room temperature for 3.5 hours. The mixture is then stirred into ice-water, the precipitate filtered off, washed with water and taken up in methylene chloride. After evaporation, there are obtained 170 mg of crude 6β-fluoro-7α-acetoxy-D-homo-4-pregnene-3,20-dione which are stirred in 5 ml of dimethylformamide with 800 mg of anhydrous sodium acetate for 8 hours at 100° C. The mixture is then stirred into ice-water, the precipitate filtered off and taken up in methylene chloride. The residue obtained after evaporation is chromatographed on silica gel. After recrystallisation from diisopropyl ether/acetone, there are obtained 50 mg of 6-fluoro-17a-acetoxy-D-homo-4,6-pregnadiene-3,20-dione of melting point 243.5°–244.5°; UV: $\epsilon_{283} = 24200$.

EXAMPLE 6

In a manner analogous to that described in Examples 4 and 5, from 17a-hexanoyloxy-D-homo-4-pregnene-3,20-dione there is obtained 17a-hexanoyloxy-D-homo-4,6-pregnadiene-3,20-dione and, from this latter D-homosteroid, there is obtained 6-fluoro-17a-hexanoyloxy-D-homo-4,6-pregnadiene-3,20-dione as an oil.

EXAMPLE 7

1.0 g of 17a-acetoxy-D-homo-4-pregnene-3,20-dione in 30 ml of dioxane is treated with 2.2 g of 2,3-dichloro-5,6-dicyano-p-benzoquinone, dry hydrogen chloride gas is led into the solution for ca. 1 minute and the mixture is then stirred at room temperature for 18 hours. The mixture is subsequently stirred into a saturated sodium bicarbonate solution, extracted with chloroform and evaporated to dryness in vacuo. The residue is chromatographed on silica gel and, after recrystallisation from diiospropyl ether/methylene chloride, there are obtained 500 mg of 17a-acetoxy-D-homo-1,4,6-pregnatriene-3,20-dione of melting point 183.5°–185.5° C; UV: $\epsilon_{220} = 11000$, $\epsilon_{252} = 9940$, $\epsilon_{300} = 10600$.

EXAMPLE 8

19.25 g of trimethylsulphoxonium iodide are dissolved in 300 ml of dimethylsulphoxide, treated with 1.375 g of powdered sodium hydroxide and stirred at room temperature for 45 minutes. 5.5 g of 17a-acetoxy-D-homo-1,4,6pregnatriene-3,20-dione are added to this solution and the mixture is stirred at room temperature for a further 5 hours. The mixture is then stirred into ice-water weakly acidified with acetic acid, the precipitate is filtered off, taken up in methylene chloride, dried and evaporated. The residue is chromatographed on silica gel and, after recrystallisation from ethyl acetate, there are obtained 2.5 g of 17a-acetoxy-1α,2α-methylene-D-homo-4,6-pregnatriene-3,20-dione of melting point 217.5°–225° C; UV: $\epsilon_{282} = 16500$.

EXAMPLE 9

2.1 g of 17a-acetoxy-1α,2α-methylene-D-homo-4,6-pregnadiene-3,20-dione in 21 ml of tertbutanol and 7 ml of methylene chloride are stirred with 4.2 g of 70% m-chloroperbenzoic acid at room temperature for 2.5 days. The mixture is then extensively concentrated in vacuo, the residue taken up in ether, washed with sodium bisulphite solution, sodium bicarbonate solution and water, dried and evaporated. The residue is chromatographed on silica gel, there being obtained 1.1 g of crude 17a-acetoxy-6α,7α-epoxy-1α,2α-methylene-D-homo-4-pregnene-3,20-dione. A sample purified by recrystallisation from diisopropyl ether/acetone melts at 235°–240.5° C; UV: $\epsilon_{237} = 12700$.

1.1 g of crude 17a-acetoxy-6α,7α-epoxy-1α,2α-methylene D-homo-4-pregnene-3,20-dione in 22 ml of acetic acid are stirred with 3.3 g of lithium chloride at room temperature for 18 hours. After precipitation with ice-water, the precipitate is filtered off, taken up methylene chloride and dried. After evaporation, there is obtained 1.0 g of crude 6β-chloro-7α-hydroxy-17a-acetoxy-1α,2α-methylene-D-homo-4-pregnene-3,20-dione; UV: $\epsilon_{237} = 11000$.

1.0 g of crude 6α-chloro-7α-hydroxy-17a-acetoxy-1α,2αmethylene-D-homo-4-pregnene-3,20-dione in 10 ml of pyridine is treated with 1.1 ml of methanesulphonic acid chloride and the mixture is stirred at room temperature for 3 hours. The mixture is then stirred into ice-water, the precipitate filtered off, taken up in methylene chloride, dried and evaporated. There is obtained 1.0 g of crude 6β-chloro-7α-mesyloxy-17a-acetoxy-1α,2α-methylene-D-homo-4-pregnene-3,20-dione.

1.0 g of crude 6β-chloro-7β-mesyloxy-17a-acetoxy-1α,2α-methylene-D-homo-4-pregnene-3,20-dione in 20 ml of dimethylformamide is stirred for 4 hours at 100° C with 5 g of anhydrous sodium acetate. After precipitation with ice-water, the precipitate is filtered off, taken up in methylene chloride and dried. After evaporation, the residue is chromatographed on silica gel and, after recrystallisation from diisopropyl ether-/acetone, there are obtained 350 mg of 6-chloro-17a-acetoxy-1α,2α-methylene-D-homo-4,6-pregnadiene-3,20-dione of melting point 207°–208.5° C; UV: $\epsilon_{283}$ = 17100.

EXAMPLE 10

10.0 g of 17a-acetoxy-D-homo-4-pregnene-3,20-dione are dissolved in 100 ml of methanol and the solution is heated under reflux for 10 minutes with 5.4 ml of pyrrolidine. The solution is then cooled to −10° C, 9.6 g of pure 17a-acetoxy-3-pyrrolidino-D-homo-3,5-pregnadien-20-one of melting point 260° C separating out.

17.8 ml of a 40% aqueous solution of formaldehyde are added over a period of 5 minutes with stirring to a solution of 9.7 g of 17a-acetoxy-3-pyrrolidino-D-homo-3,5-pregnadien-20-one in 680 ml of benzene and 1360 ml of ethanol. The mixture is stirred at room temperature for 1 hour and then evaporated to dryness in vacuo at 40° C. The residue is chromatographed on 500 g of silica gel. 2.2 g of starting material are first eluted with methylene chloride/acetone (98:2). Elution with methylene chloride/acetone (95:5) then yields 0.3 g of 17a-acetoxy-6β-hydroxy-D-homo-4-pregnene-3,20-dione and subsequently 2.9 g of 17a-acetoxy-6β-hydroxymethyl-D-homo-4-pregnene-3,20-dione. The latter D-homosteroid, after recrystallization from acetone/hexane, melts at 188°–191° C; $[\alpha]_{589}^{25°\,C}$ = +31° (c = 0.1) in dioxane); $\epsilon_{243}$ = 15400

A solution of 1.90 g of 17a-acetoxy-6β-hydroxymethyl-D-homo-4-pregnene-3,20-dione in 160 ml of dioxane is treated with 6 ml of 5-N hydrochloric acid. The solution is kept at room temperature for 2 hours and then treated with 9.2 g of sodium bicarbonate. After stirring for 15 minutes, the precipitate is filtered off and the filtrate evaporated in vacuo. There are obtained 1.8 g of a crystalline product which, after recrystallisation from acetone, yields 1.3 g of pure 17a-acetoxy-6-methylene-D-homo-4pregnene-3,20-dione of melting point 242°–243° C; $[\alpha]_{589}^{25°\,C}$ = +203° (c = 0.1 in dioxane); $\epsilon_{262}$ = 11600.

A solution of 1.20 g of 17a-acetoxy-4-methylene-D-homo-4-pregnene-3,20-dione in 40 ml of absolute ethanol is heated under reflux for 19 hours with 0.60 g of anhydrous sodium acetate and 90 mg of 5% palladium on carbon catalyst, 2 ml of a 0.5% ethanolic cyclohexene solution being added dropwise per hour. For the working-up, the mixture is filtered and the filtrate evaporated to dryness in vacuo. The residue is chromatographed on 50 g of silica gel. Elution with ether/ hexane (1:1) yields 0.7 g of pure 17a-acetoxy-6-methyl-D-homo-4,6-pregnadiene-3,20-dione of melting point 220°–221° C (from acetone/hexane); $[\alpha]_D^{25°\,C}$ = +31° (c = 0.1 in dioxane) $\epsilon_{289}$ = 25000.

EXAMPLE 11

A mixture of 386 mg of 17a-acetoxy-D-homo-4-pregnene-3,20-dione, 20 ml of dioxane, 20 mg of p-toluenesulphonic acid, 0.4 ml of methyl orthoformate and one drop of methanol is stirred at room temperature for 4 hours. There are then added a further 20 mg of p-toluenesulphonic acid, 0.4 ml of methyl orthoformate and one drop of methanol and the mixture is stirred for a further 3 hours. For the working-up, the mixture is poured on to ice-cold sodium bicarbonate solution and extracted with ether. The ether extract is washed with water and dried over potassium carbonate. After evaporation of the residue, there are obtained 400 mg of a crude product from which, after filtration through silica gel (hexane/ether; 9:1), there are isolated 320 mg of pure 17a-acetoxy-3-methoxy-D-homo-3,5-pregnadien-20-one of melting point 172°–173° C; $[\alpha]_D^{25°\,C}$ = −133° (c = 0.1 in dioxane); $\epsilon_{236}$ = 20000.

18.0 g of tetrabromomethane are added to a solution of 6.5 g of 17a-acetoxy-3-methoxy-D-homo-3,5-pregnadien-20-one in 80 ml of dioxane and 3 ml of 2,4,6-collidine. The solution is held at room temperature for 80 hours. The precipitate is filtered off and the filtrate is poured, while stirring, on to a mixture of ice-water and dilute hydrochloric acid. The precipitated product is extracted with methylene chloride, the organic extracts are washed with sodium bicarbonate solution and water, dried over sodium sulphate and evaporated. The residue, 17a-acetoxy-6-tribromomethyl-D-homo-4-pregnene-3,20-dione, is recrystallised from acetone/hexane; $\epsilon_{237}$ = 12700.

A solution of 3.2 g of 17a-acetoxy-4-tribromomethyl-D-homo-4-pregnene-3,20-dione in 50 ml of pyridine is heated to 100° C for 45 minutes. After cooling, the solution is diluted with water, the separated precipitate filtered off and recrystallised from ethanol. There are obtained 2.1 g of 17a-acetoxy-4-dibromomethylene-D-homo-4-pregnene-3,20-dione; $\epsilon_{250}$ = 10300.

A solution of 3.2 g of 17a-acetoxy-6-dibromomethylene-D-homo-4-pregnene-3,20-dione in 60 ml of dioxane and 2.5 ml of triethyleneamine is hydrogenated in the presence of 5 g of 2% palladium/strontium carbonate catalyst until 3 equivalents of hydrogen have been taken up. The catalyst is filtered off and the filtrate acidified to pH 1 with 2-N hydrochloric acid, by which means the 17a-acetoxy-6β-methyl-D-homo-4-pregnene-3,20-dione obtained is isomerised to the corresponding 6α-methyl isomer. The mixture is left to stand at room temperature for 2 hours, treated with water and extracted with methylene chloride. The organic extracts are washed neutral with sodium bicarbonate solution and water, dried over sodium sulphate and evaporated in vacuo. The residue is chromatographed on 100 g of silica gel. The fractions which are uniform according to thin layer chromatography are combined and recrystallised from acetone/hexane. There are obtained 1.4 g of pure 17a-acetoxy-6α-methyl-D-homo-4-pregnene-3,20-dione of melting point 202°–203° C; $\epsilon_{241}$ = 16300.

EXAMPLE 12

A solution of 0.80 g of D-homo-4,17-pregnadiene-3,20-dione in 80 ml of benzene and 8 ml of pyridine is treated with a solution of 0.78 g of osmium tetraoxide in 20 ml of benzene. The mixture is kept at room temperature for 1.5 hours and then evaporated at 40° C in vacuo. The residue is dissolved in 150 ml of dioxane, 50 ml of saturated sodium bisulphite solution are added and the mixture is stirred at room temperature for 30 minutes. For the working-up, the mixture is poured on to ice-cold sodium chloride solution and extracted several times with methylene chloride. The methylene chloride extracts are combined, washed with sodium carbonate solution and water, dried over sodium sulphate and evaporated in vacuo. There are obtained 1.1 g of a crude product which is chromatographed on 60 g of silica gel. Elution with methylene chloride/acetone (98:2) yields 0.45 g of pure 17α,17a-dihydroxy-D-homo-4-pregnene-3,20-dione of melting point 196°–197° C (from acetone/ isopropyl ether); $[\alpha]_D^{25°\,C} = +66°$; $\epsilon_{240} = 15900$.

A solution of 5.6 g of 17α,17a-dihydroxy-D-homo-pregn-4-ene-3,20-dione in 150 ml of acetone is treated with 1.1 ml of 70% perchloric acid and the mixture is warmed at 40° C for 4 hours. For the working-up, the mixture is poured on to icewater and extracted three times with ether. The ether extracts are washed with sodium carbonate solution and water, dried over sodium sulphate and evaporated in vacuo. The residue is chromatographed on silica gel. Elution with methylene chloride/acetone (98:2) yields 3.2 g of pure 17α,17a-(isopropylidenedioxy)-D-homo-pregn-4-ene-3,20-dione of melting point 170°–171° C (from acetone/hexane); $[\alpha]_D^{25°\,C} = +25°$; $\epsilon_{240} = 17100$.

EXAMPLE 13

A solution of 0.75 g of 2,3-dichloro-5,6-dicyano-benzoquinone in 30 ml of dioxane/6.5% HCl is added with stirring over a period of of 3 minutes to a solution of 1.0 g of 17α, 17a-(isopropylidenedioxy)-D-homo-4-pregnene-3,20-dione in 50 ml of dioxane containing 6.5% HCl. After completion of the addition, the mixture is stirred for a further 7 minutes and the cautiously treated with 15 g of sodium bicarbonate. The mixture is then stirred for 30 minutes at room temperature and finally heated under reflux for 30 minutes. The mixture is then cooled, filtered and the filtrate, after dilution with 50 ml of benzene, filtered through 20 g of Alox III. The eluates are evaporated and the residue chromatographed on silica gel. Elution with hexane/ether (4:1) yields pure 17α,17a-(isopropylidenedioxy)-D-homo-4,6-pregnadiene-3,20-dione of melting point 168°–170° C; $[\alpha]_D^{25°\,C} = -24°$; $\epsilon_{286} = 26600$.

EXAMPLE 14

4.2 g of 17a-hydroxy-D-homo-4-pregnene-3,20-dione in 85 of ethyl acetate (dried over potassium carbonate), 12.6 ml of acetic anhydride and 1.7 ml of a solution of 0.05 ml of 70% perchloric acid in 5 ml of ethyl acetate are stirred at room temperature for 3 hours under argon. After the addition of 2 ml of pyridine, the mixture is poured into 1 litre of water and extracted three times with ethyl acetate. The ethyl acetate solutions are washed twice with dilute sodium chloride solution, dried over sodium sulphate and evaporated. From methylene chloride/methanol there are obtained 3.9 g of 3,17a-diacetoxy-D-homo-3,5-pregnadien-20-one of melting point 165°–168° C; $[\alpha]_D = -133°$ (c = 0.1 in dioxane); UV: $\epsilon_{236} = 20000$.

5.6g of 3,17a-diacetoxy-D-homo-3,5-pregnadien-20-one are suspended under argon in 125 ml of ether. To this suspension are added a mixture of 8.1 g of potassium acetate, 8.1 ml of water and 73 ml of acetic acid and then 1.2 g of chlorine gas are introduced. The mixture is stirred for ca. 15 minutes at room temperature, poured on to ice-water, extracted with methylene chloride, washed with dilute sodium bicarbonate solution and water, dried over sodium sulphate and evaporated. After chromatography on silica gel, there are obtained from ethyl acetate 2.5 g of 17a-acetoxy-6β-chloro-D-homo-4-pregnene-3,20-dione of melting point 215°–216° C; $[\alpha]_D = -25°$ (c = 0.102 in dioxane); UV: $\epsilon_{239} = 14700$.

There is also obtained from acetone/hexane 0.15 g of 17a-acetoxy-6α-chloro-D-homo-4-pregnene-3,20-dione of melting point 215°–216° C; $[\alpha]_D = +33°$ (c = 0.101 in dioxane); UV: $\epsilon_{235} = 14500$.

6.15 g of crude 17α-acetoxy-6-chloro-D-homo-4-pregnene-3,20-dione in 53 ml of dioxane and 14 ml of orthoethyl formate treated with 360 mg of p-toluenesulphonic acid and the mixture is stirred at room temperature for 2.5 hours. The mixture is then added over a period of 5 minutes to a vigorously stirred suspension of 27 g of manganese dioxide in 420 ml of glacial acetic acid and 37 ml of water, the resulting mixture being stirred at room temperature for a further 2.5 hours. The mixture is subsequently filtered and the filtrate worked-up with water and methylene chloride in the usual manner. After chromatography on silica gel, there are obtained 900 mg of 17a-acetoxy-6-chloro-D-homo-4,6-pregnadiene-3,20-dione of melting point 228°–229° C; UV: $\epsilon_{284} = 22500$; $[\alpha]_D = +16°$ (c = 0.102 in dioxane).

The starting material can be prepared as follows:

2.0 g of 17a-acetoxy-D-homopregn-4-ene-3,20-dione is dissolved in 100 ml of 5% methanolic potassium hydroxide and the solution is stirred at room temperature for 5 hours. It is then poured on to ice-water and extracted with methylene chloride. The methylene chloride extracts are washed with water, dried over sodium sulphate and evaporated in vacuo. The residue is recrystallised from acetone/hexane and yields pure 17a-hydroxy-D-homo-pregn-4-ene-3,20-dione of melting point 181°–183° C; $\epsilon_{241} = 15800$; $[\alpha]_D^{25°\,C} = +66°$ (c = 0.1 in dioxane).

EXAMPLE 15

A solution of 300 mg of 17a-acetoxy-6α,7α-epoxy-D-homo-4-pregnene-3,20-dione in 12 ml of acetic acid is saturated at room temperature with hydrogen chloride gas and left to stand for 4 hours. The mixture is evaporated in vacuo, the residue taken up in toluene and the solution again evaporated in vacuo. Chromatography on silica gel yields 150 mg of 17a-acetoxy-6-chloro-D-homo-4,6-pregnadiene-3,20-dione of melting point 228°–229° C (from acetone/hexane); $[\alpha]_D = +16°$ (c = 0.102 in dioxane); UV: $\epsilon_{284} = 22500$.

EXAMPLE 16

A solution of 400 mg of 17a-acetoxy-6α,7α-epoxy-D-homo-4-pregnene-3,20-dione in 10 ml of glacial acetic acid is treated with 0.425 ml of 30% hydrogen bromide in glacial acetic acid and the mixture is stirred at room temperature under argon for 4 hours. The mixture is evaporated in vacuo, the residue taken up in toluene and the solution again evaporated in vacuo. After chromatography on silica gel, there are obtained from acetone/hexane 235 mg of 17a-acetoxy-6-bromo-D-homo-4,6-pregnadiene-3,20-dione of melting point 165°–166° C (decomposition); $[\alpha]_D = +47°$ (c = 0.103 in dioxane); UV: $\epsilon_{287} = 19900$.

EXAMPLE 17

A solution of 840 mg of 17a-acetoxy-6-chloro-D-homo-4,6-pregnadiene-3,20-dione in 10 ml of alcohol-free chloroform is treated at 0° C with 2.0 ml of a 1.1-M solution of chlorine in carbon tetrachloride and the mixture is stirred at 0° C for 1 hour. The mixture is then evaporated, the residue taken up in hexane and the turbid solution again evaporated. The oil obtained is left to stand at room temperature for 2 hours in 10 ml of pyridine. The mixture is then poured into 2-N hydrochloric acid and extracted three times with methylene chloride. The methylene chloride extracts are washed twice with dilute sodium chloride solution, dried and evaporated. Chromatography of the crude product on silica gel yields 225 mg of 17a-acetoxy-4,6-dichloro-D-homo-4,6-pregnadiene-3,20-dione of melting point 254°–255° C; $[\alpha]_D = +153°$ (c = 0.104 in dioxane); UV: $\epsilon_{298} = 15500$.

EXAMPLE 18

500 mg of 17a-acetoxy-6-chloro-D-homo-4,6-pregnadiene-3,20-dione and 340 mg of 2,3-dichloro-5,6-dicyano-benzoquinone in 10 ml of absolute tetrahydrofuran containing 0.2% hydrogen chloride gas are stirred at 0° C for 6 hours under argon. 2.5 g of anhydrous sodium carbonate are then added and the mixture is stirred at room temperature for 16 hours. The mixture is then heated to boiling for a short time, cooled and filtered. The filtrate is decolourised on neutral aluminium oxide (Activity II) and then evaporated. Chromatography of the crude product on silica gel yields 17α-acetoxy-6-chloro-D-homo-1,4,6-pregnatriene-3,20-dione; UV: $\epsilon_{229} = 11300$; $\epsilon_{253} = 10200$; $\epsilon_{302} = 10400$.

EXAMPLE 19

3.3 g of D-homopregna-4,17-diene-3,20-dione are dissolved in 50 ml of absolute toluene and the solution is cooled to 10° C. There are then added while stirring at 10° C over a period of 20 minutes 65 ml of a 0.4-M suspension of a methylmagnesium iodide complex in tetrahydrofuran containing 125 mg of cuprous chloride. After the addition of the Grignard suspensin, the mixture is stirred for a further 15 minutes at 10° C and then treated over a period of one minute at 10°–15° C with 1.5 ml of acetyl chloride in 12 ml of tetrahydrofuran. After a further 15 minutes, the mixture is cooled to 10° C and decomposed by the addition of a mixture of 20 ml of 25% ammonium chloride solution and 6 ml of 25% sodium thiosulphate solution. The aqueous layer is extracted with benzene, the organic extracts are washed with ammonium chloride solution and water, dried over sodium sulphate the evaporated in vacuo. The residue is dissolved in 120 ml of ether and treated with a solution of 2.5 g of m-chloroperbenzoic acid in 50 ml of ether. The mixture is kept at room temperature for 6 hours, then washed successively with sodium thiosulphate. solution, sodium carbonate solution and water, dried over sodium sulphate and evaporated in vacuo. The residue is dissolved in 100 ml of methanol and, after the addition of 1.5 g of potassium carbonate in 30 ml of water, saponified by boiling for 3 hours under argon. The solution is then treated with 500 ml of ice-water and extracted with methylene chloride. The methylene chloride extracts are washed neutral with water, dried over sodium sulphate and evaporated in vacuo. The residue is chromatographed on silica gel with methylene chloride/acetone. The fractions which are uniform according to thin-layer chromatography are combined and, after recrystallisation from acetone/hexane, yield pure 17α-methyl-17a-hydroxy-D-homo-pregn-4-ene-3,20-dione; $\epsilon_{240} = 16400$.

EXAMPLE 20

A mixture of 2.0 g of 17a-acetoxy-5α-bromo-6β-fluoro-D-homopregnane-3,20-dione, 2.0g of anhydrous sodium acetate and 100 ml of 95% ethanol is heated under reflux for 30 minutes. The solvent is evaporated in vacuo at 40° C, the residue treated with water and extracted with ether. The other extract is washed with water, dried over sodium sulphate and evaporated. The residue is crystallised from acetone/hexane and yields pure 17a-acetoxy-6β-fluoro-D-homopregn-4-ene-3,20-dione; $\epsilon_{233} = 12800$.

The starting material is prepared as follows:

17a-Acetoxy-3β-hydroxy-D-homopregn-5-ene-3,20-dione is converted using N-bromoacetamide and anhydrous hydrogen fluoride in methylene chloride/tetrahydrofuran at −70° C into 17a-acetoxy-5α-bromo-6β-fluoro-3β-hydroxy-D-homopregnan-20-one which, by oxidation with chromium trioxide, yields 17a-acetoxy-5α-bromo-6β-fluoro-D-homopregnane-3,20-dione.

EXAMPLE 21

A solution of 2.0 g of 17a-acetoxy-D-homopregn-4-ene-3,20-dione and 1.40 g of 2,3-dichloro-5,6-dicyano-benzoquinone in 100 ml of dioxane is heated under reflux for 24 hours. For the working-up, the mixture is evaporated in vacuo, treated with water and extracted with ether. The organic extracts are washed twice with dilute sodium hydroxide solution and then three times with water, dried over sodium sulphate and evaporated to dryness in vacuo. The residue is chromatographed on 50 g of silica gel. Elution with ether/-hexane (3:1) yields pure 17a-acetoxy-D-homopregna-1,4-diene-3,20-dione of melting point 209°–210° C (from acetone/hexane); $\epsilon_{243} = 16000$; $[\alpha]_D^{25°\,C} = +25°$ (c = 0.1 in dioxane).

EXAMPLE 22

A solution of 1.5 g of 20,20-ethylenedioxy-5α-hydroxy-6β,17a-dimethyl-D-homopregnan-3-one and 1.0 g of p-toluenesulphonic acid in 45 ml of acetone and 5 ml of water is heated under reflux for 30 minutes. The mixture is cooled, poured on to ice-water and extracted with methylene chloride. The methylene chloride extract is washed neutral with sodium carbonate solution and water, dried over sodium sulphate and evaporated in vacuo. The residue is chromatographed on silica gel using methylene chloride/hexane. The fractions which are uniform according to thin-layer chromatography are combined and evaporated to yield 6α,17a-dimethyl-D-homopregn-4-ene-3,20-dione which is recrystallised from acetone/hexane; $\epsilon_{241} = 15600$.

The starting material is prepared as follows:

3β-Hydroxy-D-homopregna-5,17-dien-20-one is treated with lithium in ammonia and subsequently reacted with methyl iodide to yield 3β-hydroxy-17a-methyl-D-homopregna-5-en-20-one. Treatment of the latter with ethyleneglycol in toluene while heating yields 20,20-ethylenedioxy-3β-hydroxy-17a-methyl-D-homopregn-5-ene which is reacted with m-chloroperbenzoic acid to give 20,20-ethylenedioxy-5α,6α-epoxy-3β-hydroxy-17a-methyl-D-homopregnane. Reaction of the latter with methylmagnesium iodide gives 20,20-ethylenedioxy-3β,5α-dihydroxy-6β,17a-dimethyl-D-homopregnane which is oxidised with chromium trioxide according to the Jones' procedure to yield 20,20-ethylenedioxy-5α-hydroxy-6β,17a-dimethyl-D-homopregnan-3-one.

EXAMPLE 23

A solution of 2.50 g of p-toluenesulphonic acid and 2.0 g of 17a-hydroxy-D-homopregn-4-ene-3,20-dione in 70 ml of caproic acid anhydride is warmed to 40° C for 3 hours. The solution is then treated with a mixture of 2.8 ml of concentrated hydrochloric acid and 280 ml of methanol and heated under reflux for 1 hour. The mixture is evaporated to half volume in vacuo, then poured on to ice-water and extracted with methylene chloride. The methylene chloride extract is washed neutral with sodium carbonate solution and water, dried over sodium sulphate and evaporated in vacuo. The residue, 17a-caproyl-D-homopregn-4-ene-3,20-dione, is recrystallised from isopropyl ether; $\epsilon_{240}$ = 16700.

EXAMPLE 24

1.4 g of 17a-acetoxy-6β-fluoro-D-homopregn-4-ene-3,20-dione are dissolved in 50 ml of glacial acetic acid and the solution is treated with 0.5 ml of 30% hydrogen bromide in glacial acetic acid. The solution is kept at room temperature for 1 hour, then treated with 3 ml of pyridine, poured on to ice-water and extracted with methylene chloride. The methylene chloride extract is washed neutral with ice-cold dilute sodium hydroxide solution and water, dried over sodium sulphate and evaporated in vacuo. The residue is recrystallised from acetone/hexane to yield pure 17a-acetoxy-6α-fluoro-D-homopregn-4-ene-3,20-dione; $\epsilon_{236}$ = 14400.

We claim:

1. A D-homosteroid of the formula

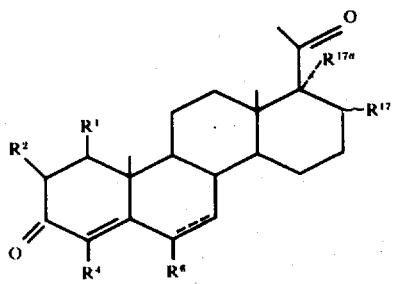

wherein each of $R^1$ and $R^2$ is hydrogen or together are a carbon to carbon bond; $R^4$ is hydrogen or chloro; $R^6$ is hydrogen, fluoro, chloro, bromo or methyl; $R^{17}$ is hydrogen, methyl, methylene, $C_{1-7}$-alkanoyloxy or alkyloxy; $R^{17a}$ is methyl or $C_{1-7}$ alkanoyloxy provided that at least one of $R^{17}$ or $R^{17a}$ is $C_{1-7}$ alkanoyloxy and wherein the broken line in the 6,7-position denotes an optional carbon to carbon bond, provided that when $R_1$ and $R_2$ are each hydrogen and $R_6$ is H or methyl, there is a double bond at the 6,7-position.

2. A D-homosteroid according to claim 1 wherein each of $R^1$, $R^2$, $R^4$, and $R^{17}$ is hydrogen and $R^{17a}$ is $C_{1-7}$ alkanoyloxy.

3. A D-homosteroid according to claim 1 wherein $R^6$ is chloro or methyl; and $R^{17a}$ is alkanoyloxy containing from 1 to 7 carbon atoms.

4. The compound of claim 1 which is 17a-acetoxy-D-homo-4,6-pregnadiene-3,20-dione.

5. The compound of claim 1 which is 6-fluoro-17a-acetoxy-D-homo-4,6-pregnadiene-3,20-dione.

6. The compound of claim 1 which is 17a-hexanoyloxy-D-homo-4,6-pregnadiene-3,20-dione.

7. The compound of claim 1 which is 6-fluoro-17a-hexanoyloxy-D-homo-4,6-pregnadiene-3,20-dione.

8. The compound of claim 1 which is 17a-acetoxy-D-homo-1,4,6-pregnatriene-3,20-dione.

9. The compound of claim 1 which is 17a-acetoxy-6-methyl-D-homo-4,6-pregnadiene-3,20-dione.

10. The compound of claim 1 which is 17a-acetoxy-6 β-chloro-D-homo-4-pregnene-3,20-dione.

11. The compound of claim 1 which is 17a-acetoxy-6 β-chloro-D-homo-4-pregnene-3,20-dione.

12. The compound of claim 1 which is 17a-acetoxy-6-chloro-D-homo-4,6-pregnadiene-3,20-dione.

13. The compound of claim 1 which is 17a-acetoxy-6-bromo-D-homo-4,6-pregnadiene-3,20-dione.

14. The compound of claim 1 which is 17a-acetoxy-4,6-dichloro-D-homo-4,6-pregnadiene-3,20-dione.

15. The compound of claim 1 which is 17a-acetoxy-6-chloro-D-homo-1,4,6-pregnatriene-3,20-dione.

16. The compound of claim 1 which is 17a-acetoxy-6 β-fluoro-D-homopregn-4-ene-3,20-dione.

17. The compound of claim 1 which is 17a-acetoxy-D-homopregna-1,4-diene-3,20-dione.

18. The compound of claim 1 which is 17a-acetoxy-6 β-fluoro-D-homopregn-4-ene-3,20-dione.

* * * * *